United States Patent [19]

Lindauer et al.

[11] 4,184,099

[45] Jan. 15, 1980

[54] COMPOSITION FOR SLOW RELEASE OF VOLATILE INGREDIENTS AT HIGH TEMPERATURE; AND ARTICLE COMPRISING SAME

[75] Inventors: Jerome I. Lindauer, Hillsdale, N.J.; Marina Munteanu, New York; Sharon Reich, Briarwood, both of N.Y.; Enrique Pelliza, Bogota, Colombia

[73] Assignee: International Flavors & Fragrances Inc., New York, N.Y.

[21] Appl. No.: 913,698

[22] Filed: Jun. 8, 1978

Related U.S. Application Data

[63] Continuation-in-part of Ser. No. 791,403, Apr. 27, 1977, abandoned.

[51] Int. Cl.² .................... C09F 5/00; H01J 5/00; H01J 21/00
[52] U.S. Cl. .................... 313/315; 106/243; 252/522; 260/404.5
[58] Field of Search .................... 252/522; 260/18 PN, 260/404.5 R; 106/243; 21/120; 313/310, 317, 315

[56] References Cited

U.S. PATENT DOCUMENTS

| | | | |
|---|---|---|---|
| 3,148,125 | 9/1964 | Strianse et al. | 424/65 |
| 3,303,046 | 2/1967 | Chebiniak et al. | 428/307 |
| 3,396,180 | 8/1968 | Floyd et al. | 260/404.5 |
| 3,474,176 | 10/1969 | Freeman | 424/331 |
| 3,725,311 | 4/1973 | Grubb | 252/522 |
| 3,763,347 | 10/1973 | Whitaker | 219/275 |
| 3,926,655 | 12/1975 | Miles | 106/270 |
| 4,051,159 | 9/1977 | Tsoucalas et al. | 260/404.5 R |

FOREIGN PATENT DOCUMENTS

1176992  4/1959  France .

*Primary Examiner*—Theodore Morris
*Attorney, Agent, or Firm*—Arthur L. Liberman; Franklin D. Wolffe

[57] ABSTRACT

Bodies which are formed compositions of Versalon ® type polyamide resin containing from about 35% up to about 70% by weight of highly volatile materials such as perfumes, odorants, insecticides, bactericides, and animal repellents which are able to act in a very diluted vapor state in the air for relatively long periods of time, are described. The highly volatile substances are released in a controlled manner over a long period of time. The molecular weight of the resin is between 9,000 and 12,000, and its softening point varies from 120° C. up to 400° C. In addition, articles are described incorporating said composition and, as part of the instant invention, a light bulb coated with a toroidal article which consists essentially of said composition, is included.

The method of our invention comprises heating Versalon ® polyamide resin (Note 1) having a molecular weight of from 9,000 up to 12,000 until it is pourable and stirrable, e.g., to a temperature of between 120° C. and 400° C., and then blending from 35 up to 70% of a highly volatile ingredient such as a perfume oil, an insecticide composition, a bactericide composition, or an animal repellent composition, into the melt until a uniform mixture is obtained, and cooling the mixture to solidify it as such or in a toroidal state, preferably rapidly as by quenching in cold water. The product so obtained is then formed into an article such as a coating on a substrate such as an electric light bulb. Alternatively, one or more volatile ingredients are blended into the resin in the feed line of a molding machine in which the resin bodies containing said volatile ingredients are fashioned directly.

Note 1: Versalon ® is a trademark of the General Mills Corporation of Minneapolis, Minnesota.

12 Claims, 5 Drawing Figures

COMPOSITION FOR SLOW RELEASE OF VOLATILE INGREDIENTS AT HIGH TEMPERATURE; AND ARTICLE COMPRISING SAME

Related Copending Patent Applications

This application is a continuation-in-part of application for U.S. Pat. Ser. No. 791,403 filed on Apr. 27, 1977 now abandoned.

BACKGROUND OF THE INVENTION

U.S. Pat. No. 3,926,655 issued on Dec. 16, 1975, and filed on Sept. 23, 1974 (continuation-in-part of application for Patent Ser. No. 328,425 filed on Jan. 31, 1973, now abandoned) discloses the formation of a clear, relatively rigid Versamid ® polyamide resin body containing perfume oil which can be made without substantial amounts of added cosolvent by proper selection of the polyamide resin and by following certain preparative procedures. U.S. Pat. No. 3,926,655 more specifically describes bodies of clear, substantially cosolvent-free Versamid ® type polyamide resin containing perfume oil in the range of small amounts (up to 30% by weight) that yields a clear resin. It is indicated therein that perfumed articles may be in the form of jewelry, decorative castings, coatings on substrates and the like. The molecular weight range of Versamid ® polyamide resin used in U.S. Pat. No. 3,926,655 is from 6,000 up to 9,000, but the maximum percentage of perfume oil contained therein is indicated to be 30%.

The instant invention takes advantage of the unexpected, unobvious and advantageous effect of the capability of Versalon ® type polyamides having molecular weights in the range of from 9,000 up to 12,000 which can incorporate from 35% up to 70% by weight of total composition of volatile ingredients, including perfume oils. Thus, a 30% increase in the molecular weight of the resin gives rise to the unexpected result that up to and even more than double the amount of volatile ingredient can be incorporated therein and can be given off in a controlled, steady state release rate.

U.S. Pat. No. 3,148,125 issued on Sept. 8, 1964, (filing date Mar. 22, 1961) discloses cosmetic lipsticks which besides carrying color for staining the lips and a vehicle for the color, have a body sufficiently strong and stable to permit its use as an applicator and yet capable of rubbing off onto the lips a film adapted to color and protecting the lips and leaving an attractive, well-groomed appearance. The materials are indicated to be fabricated using polyamide resins having softening points of between 90° and 120° C. More specifically, U.S. Pat. No. 3,148,125 discloses a syneresis-resistant cosmetic coloring stick which comprises a gel, the base of which is a polyamide resin which in the absence of other ingredients would be solid, a dye, and a fatty acid ester wherein the acid contains from 12-18 carbon atoms, and an anhydrous lower aliphatic alcohol. The molecular weight of the polyamide resin used in this case is about 8,000. There is no suggestion in U.S. Pat. No. 3,148,125 of the instant invention.

French Pat. No. 1,176,992 published on Apr. 17, 1959, discloses a process for the fabrication of "solid perfumes". The process in the French patent consists of massive incorporation in a natural or synthetic resin of a perfume in its liquid form whether synthetic or whether providing the fixation of a natural perfume by means of a liquid adjuvant. No specific resins or specific resin classes or molecular weight ranges or softening point ranges or quantities of perfume oils are disclosed in French Pat. No. 1,176,992, however.

U.S. Pat. No. 3,303,046 issued on Feb. 7, 1967, (filing date Dec. 30, 1963) discloses a method for producing porous plastic materials having contained in the pores a liquid which is expressible in response to pressure. In the primary embodiment of the invention of U.S. Pat. No. 3,303,046, an organic dye is dissolved in a plasticizer so that the product may be employed as a transfer elememt. It is mentioned at Column 2, lines 46-54 that the active ingredients other than ink-forming dyes or toners may be incorporated into the plasticizer to alter the character and use of the end product; for example, medicines, antiseptics, deodorants, perfumes, waxes, and polishes.

Nothing in U.S. Pat. No. 3,303,046, however, suggests the article, process or composition of the instant invention.

Low temperature extrudable odor neutralizing compositions comprising a polymer of 80-98% polyvinyl chloride, 2-20% polyvinyl acetate and 0-20% polyvinyl alcohol, a plasticizer, a filler to maintain a dry mixture and a volatile odor neutralizing or modifying agent are described in U.S. Pat. No. 3,725,311 issued on Apr. 3, 1973 (filing date May 15, 1972; continuation of Ser. No. 10,993 filed on May 15, 1972, abandoned). The instant invention is neither explicitly nor implicitly described in U.S. Pat. No. 3,725,311, and it is notable that no mention or suggestion is made of the use of polyamides therein.

THE INVENTION

Figure 1:
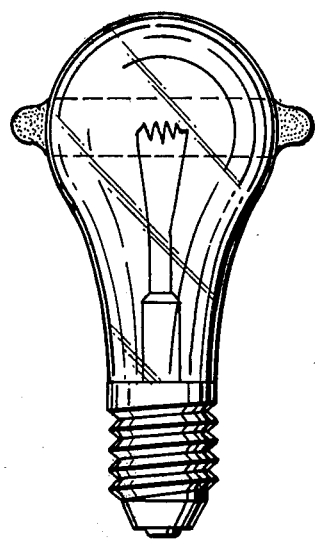
FIG. 1 illustrates the use of the composition of this invention in a perfumed article wherein the composition of this invention is formed into a toroid, and the toroid is wrapped around the surface of an electric light bulb.
Figure 2:
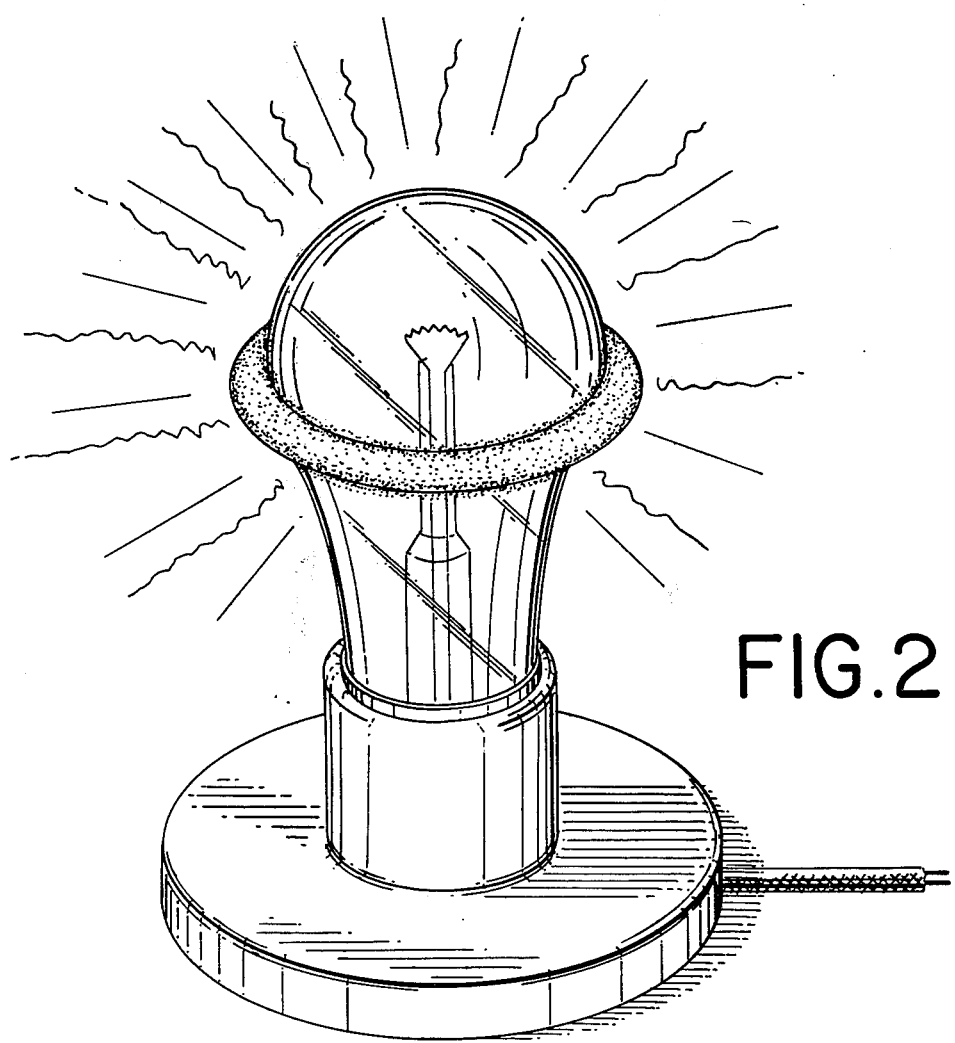
FIG. 2 illustrates the article of FIG. 1 in operation.
Figure 3:
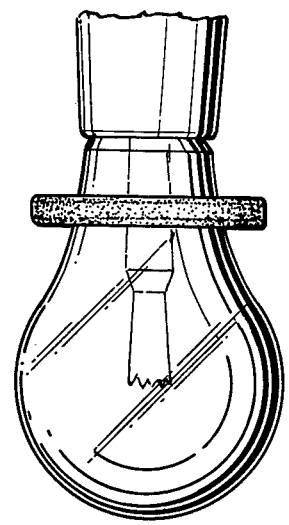
FIG. 3 is a photograph of an energized 100 watt light bulb bearing a toroid consisting of Versalon ® 1200 containing 40% perfume which light bulb has been energized for a period of five hours.
Figure 4:
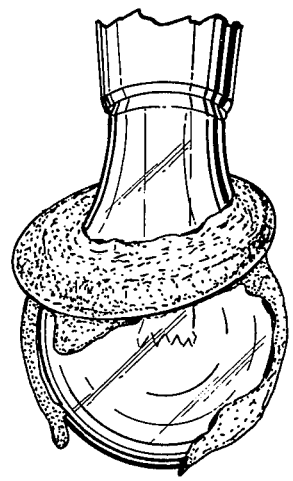
FIG. 4 is a photograph of an energized 100 watt light bulb bearing a toroid consisting of 40% perfume-containing Versamid ® 930 resin which light bulb has been energized for a period of five hours.

It has now been discovered that a relatively rigid Versalon ® type polyamide resin body containing such volatile substances as perfume oil, odorants, insecticides, bactericides, and animal repellents can be made with a very high volatile substance loading content and consequential extended period of time of steady state delivery of volatile substance into the surrounding atmosphere by proper selection of polyamide resins and by following certain preparative procedures as set forth herein below.

The resins used in the invention are able to hold between 35 and 70% of volatile substance. In general, the Versalon ® type polyamide resins having thi desired property are fatty polyamides based on the condensation of polyamides, especially diamines and triamines, with relatively high molecular weight dibasic acids, especially of the type which result from dimerization of diunsaturated carboxylic acids, e.g., the condensation products of dimerized linoleic acid and ethylene diamine. These polyamides have molecular weights within the range of from about 9,000 up to about 12,000. They are characterized by substantial retention of their room temperature hardness on heating until very near the melting or softening temperature which is relatively sharp., e.g., over a range of 10°–15° C., and within the range of from about 120° up to 400° C., depending upon the molecular weight, and by a sharp decrease in viscosity at temperatures above the melting or softening point or range. Methods of making such resins are disclosed in U.S. Pat. No. 3,396,180 issued on Aug. 6, 1968. In contrast, some well known polyamide resins of the nylon type, e.g., nylon 6, which are not suitable for the present invention have higher molecular weights but do not retain the volatile substances in any way or manner near the retention properties of the Versalon ® type polyamide resins discribed herein. This is probably due to the fact that the components of the mixture are not cosoluble with one another.

The advantages of using the Versalon ® type polyamide resin as described herein are as follows:

(1) The resulting product can emit the contained volatile substance for a longer period of time because of being able to incorporate rather high (35–70%) amounts of volatile materials in a rigid, hard, non-sticky body;

(2) The volatile material is subject to a controlled steady state release for the following reasons and under the following conditions:

(a) The vaporization rate is a function of temperature and is almost nil at room temperature; and the product works only when subject to elevated temperatures;

(b) The vaporization rate of the active substance(s) is relatively slow and constant over an extended period of time (as opposed to the use of the molecular weight range of Versamid ® polyamide resins of U.S. Pat. No. 3,926,655). Furthermore, the evaporation of the active substance remains at a constant rate during the employment of the composition in the environment intended (e.g., a light bulb);

(c) Since the product works only when heat is applied, the entire amount of active substance is used in a controlled manner thereby eliminating waste of said active volatile substance.

A resin suitable for use in the invention is made by reacting dimerized linoleic acid with ethylene diamine to produce a product of the formula:

HO (—OC—R—CONHR$^1$—NH)$_n$H in which R is a hydrocarbon group of an indeterminate configuration and R$^1$ is —CH$_2$CH$_2$—and which has the following typical properties:

| | |
|---|---|
| Softening Point (Ball and Ring) | 200° C. |
| Viscosity (Brookfield) | |
| Poises at 240° C. | 30–50 |
| Tensile Strength (p.s.i.) | 3,000 |
| Flexibility (percent elongation) | 500 |

It is a high performance, thermoplastic polymer having a relatively sharp melting point and is thermoplastic with a narrow heat seal range. It exhibits good adhesion to a variety of substrates and can be applied to substrates from solution or from a melt. Thin films show good flexibility. The resin is conveniently prepared for commercial use in diced form for supplying either batch heating vessels or molding machines. Such a resin is available commercially from General Mills, Inc., under the following names:

| | Ball and Ring Softening Point |
|---|---|
| Versalon ® 1135 | 135° C. |
| Versalon ® 1138 | 138° C. |
| Versalon ® 1140 | 140° C. |
| Versalon ® 1164 | 164° C. |
| Versalon ® 1185 | 183° C. |
| Versalon ® 1200 | 200° C. |

Resins having these properties are excellently suitable for the present invention.

Figure 5:
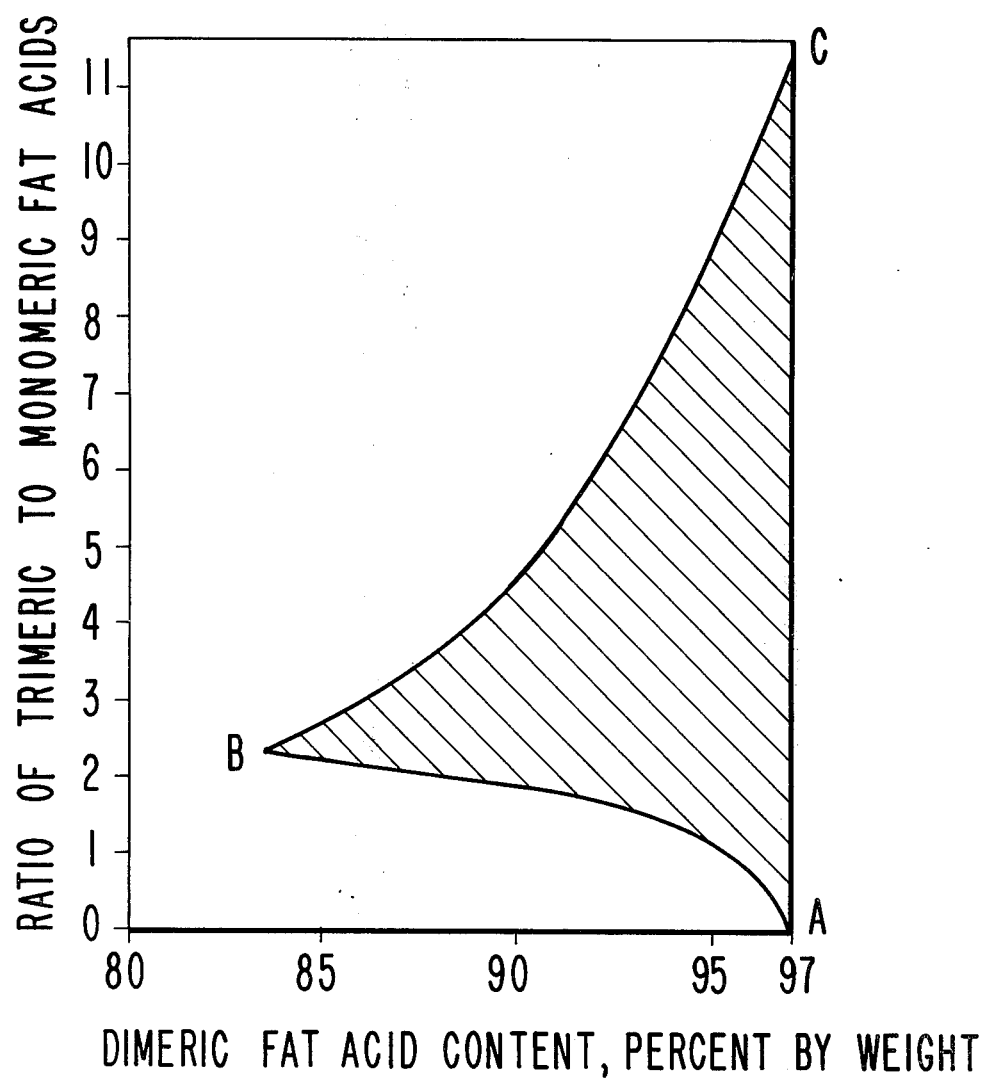
FIG. 5 is a graphical representation showing the required combination in the Versalon ® type polyamid resins useful in our invention of dimer content and trimer:monomer ratio.

Such Versalon ® resins, more specifically, are produced according to U.S. Pat. No. 3,396,180 issued on Aug. 6, 1968 and are reaction products of ethylenediamine and distilled mixtures of monomeric, dimeric and trimeric fatty acids, the ratio of dimeric fatty acid content: trimeric fatty acid content: monomeric fatty acid content being defined substantially within the area ABC of FIG. 1 of U.S. Pat. No. 3,396,180. FIG. 1 of U.S. Pat. No. 3,396,180 is identical to FIG. 5 herein:

The desirable combination of properties of the Versalon ® ethylenediamine polyamide (of polymeric fat acid) having a particular dimeric fat acid content with a particular trimeric to monomeric fat acid ratio are shown in FIG. 5 which is a graphical representation showing the required combination of dimer content and trimer to monomer ratio. In FIG. 5, the products prepared from polymeric fat acid having the combination falling substantially within the shaded areas bounded by curve ABC will provide the required combination of softening point, viscosity, elongation, tensile strength, density, heat seal range and other properties necessary to practice the instant invention. These polyamide compositions are prepared by reacting ethylenediamine with the desired polymeric fat acid. Approximately one molar equivalent of amine is employed per molar equivalent of carboxyl group present. The reaction is carried out in the range of 150°–300° C. at atmospheric pressure for about 1 to 5 hours, during which time the water of condensation is allowed to distill off, and following which a vacuum (about 20 mm. Hg) is applied and the product maintained at 150°–300° C. for ½ to 3 hours. The required polymeric fat acid is one having a particular trimer to monomer ratio for each level of dimeric fat acids content. Defining the exact trimer:monomer ratio for each level of dimeric fat acids contained requires an appropriate mathematical relationship most accurately depicted in FIG. 5. The ordinate of FIG. 5 is a scale of trimer:monomer ratio. The abscissa of FIG. 5 is a scale of dimeric fat acids content in percent weight. The area bonded substantially within the curve ABC includes those polyamides, defined as Versalon ® in the present invention which are considered satisfactory for the purpose of carrying out the instant invention. The area essentially outside the area ABC contains those polyamides which are not satisfactory for the purposes of carrying out this invention. Those products falling generally below the boundary ABC fail as being brittle, non-flexible and unable to withstand the heat and solvent power of the volatile ingredients. Those falling generally above the boundary BC fail as having a melt viscosity of a level impractically high or as being intractable gel polymers. As is apparent from the curve ABC at substantially 84% dimer content, the trimer to monomer ratio is extremely narrow being substantially 2.3. As the dimer content increases, this ratio expands to a widening range. At about 97% dimer acid content, the criticality of the trimer to monomer ratio becomes almost non-existent. As a practical matter, at 97% dimer acid content a general range of the ratio of 0.3 to about 10 may be given. The term "polymeric fat acids" as used herein is intended to be generic to polymerized acids obtained from "fat acids". The term "fat acids" is intended to include saturated, ethylenically unsaturated and acetylenically unsaturated naturally occurring and synthetic monobasic aliphatic acids containing from 8 to 24 carbon atoms. The saturated, ethylenically unsaturated and acetylenically unsaturated fat acids are generally polymerized in somewhat different techniques, but because of the functional similarity of the polymerization products, they are generally referred to as "polymeric fat acids". The polymerization techniques for these fat acids and subsequent formation of the polyamide Versalon ® type resins is specifically set forth at columns 2, 3 and 4 of U.S. Pat. No. 3,396,180 issued on Aug. 6, 1968.

The fragrances suitable for the present invention, sometimes called perfume oils, are complex mixtures of volatile compounds including esters, ethers, aldehydes, nitriles, alcohols, unsaturated hydrocarbons, e.g., terpenes, and the like which are well known to persons skilled in the fragrance art and need not be further identified. Their use as to type and proportion in the present invention is limited only by solubility in the resin to produce a product which will controllably release said perfume at a steady rate when contained in the resin in an amount of from 35-70%.

Other volatile substances such as insecticides, bactericides, odorants and animal repellents useful in the present invention are well known to those skilled in the art. Their use as to type and proportion in the present invention is limited only by solubility in the resin to produce a product which will controllably release such a volatile substance when contained in the resin in an amount of from 35 up to 70%. An example of animal repellent useful in the present invention is methyl-n-nonylketone as described in U.S. Pat. No. 3,474,176 issued on Oct. 21, 1969.

The process of making the resin bodies containing the volatile substance, e.g., the perfume oil, the odorant, the insecticide, the bactericide and the animal repellent, of our invention comprises melting the resin by heating it until sufficiently molten to be stirrable and pourable. Where a resin having the properties specified above is used, this condition obtains when the temperature is within the range of from about 120° C. up to about 400° C.; preferably between about 190° and 215° C. The volatile substance such as the perfume oil is added to the liquid resin and blended therewith by stirring or other mechanical agitation until a uniform mixture or blend is formed. Although not necessary for the practice of our invention, no cosolvent for the resin and the volatile substance need be added at any time during the process. The mixture is cooled promptly after thorough mixing to solid condition, preferably rapidly as by quenching in cold water or by pouring into or bringing into contact with a cold metal surface to which it is not adherent. The product obtained by this process is capable of releasing the volatile substance at a controlled rate over a very long period of time, has a highly polished surface and retains a substantial proportion of the volatile substance for months. In the case of perfume oils, the product has a strong fragrance that faithfully represents the odor of the perfume oil, particularly since the resin used in this case has a substantially non-existent inherent odor.

The articles containing the volatile materials of the present invention may be formed into a wide variety of useful objects such as coated electric light bulbs where the heat of the lighted filament increases the volatility and rate of transfer to the atmosphere of the volatile substance from the resin coating. Such electric light bulbs can be, for example, scented with pine oil and, in addition, combined with animal repellents or insecticides.

The portion of volatile substance, e.g., perfume oil to resin may vary from 35% up to the maximum amount that the resin can contain and still appear in a dry state which is usually of the order of about 70%. In general, it is preferred to use about 35 up to 50% which is an optimum value balancing the proportion of volatile substance contained in the product against the length of time period over which the objects are useable for giving off or emitting the volatile substance into the atmosphere.

The following examples A, B and C illustrate the method for preparing the Versalon ® resins useful in our invention. The following examples I-III illustrate the method and products of the invention. The examples are intended to be illustrative and the invention is limited only is indicated in the appended claims. All proportions are in parts by weight unless otherwise indicated.

EXAMPLE A

Into a glass reactor equipped with thermometer, stirrer and distillation head are placed the polymeric fat acids from tall oil. After heating to 60° C., a molar equivalent amount of ethylenediamine is added. The heat is gradually raised over a period of two hours to 205° C., during which time most of the water of reaction is removed. The temperature is held at 205° C. for two hours. Water pump vacuum is then applied (10 to 20 mm. Hg) and held at 205° C. for an additional two hours. The resulting product is then analyzed and tested and the data reported in the attached Table I.

TABLE I

| Run No. | Percent M (Monomeric fat acid) | Percent D (Dimeric fat acid) | Percent T (Trimeric fat acid) | T/M | Acid No. | Amine No. | B & R M. Pt. °C. | Visc. 160° C. Poises | Visc. 205° C. Poises | Tensile Strength, P.s.i. | Percent Elong. | Heat Seal* Range, °C. |
|---|---|---|---|---|---|---|---|---|---|---|---|---|
| 1A | 3 | 90 | 7 | 2.33 | 4.14 | 6.65 | 103.5 | 185 | 30 | 1,655 | 425 | 75–155 |
| 1B | 3 | 90 | 7 | 2.35 | 5.85 | 2.35 | 110 | 330 | 60 | 2,266 | 440 | 86–155 |
| 2A | 2 | 92 | 6 | 3 | 3.92 | 6.35 | 112.8 | 260 | 52.5 | 2,140 | 460 | 80–160 |
| 2B | 2 | 92 | 6 | 3 | 5.1 | 3.55 | 110 | 450 | 105 | 2,446 | 500 | 90–170 |
| 3 | 2 | 93.6 | 4.2 | 2.1 | 5.1 | 3.85 | 114 | 255 | 40 | 2,151 | 390 | 80–155 |
| 4 | 2.5 | 90.3 | 7.1 | 2.84 | 5.45 | 2.55 | 111.3 | 555 | 80 | 2,161 | 540 | 80–165 |

TABLE I-continued

| Run No. | Percent M (Monomeric fat acid) | Percent D (Dimeric fat acid) | Percent T (Trimeric fat acid) | T/M | Acid No. | Amine No. | B & R M. Pt. °C. | Visc. 160° C. Poises | Visc. 205° C. Poises | Tensile Strength, P.s.i. | Percent Elong. | Heat Seal* Range, °C. |
|---|---|---|---|---|---|---|---|---|---|---|---|---|
| 5 | 2.16 | 95.68 | 2.16 | 1 | 5.25 | 2.25 | 112 | 400 | — | 1,050 | 775 | 76–155 |
| 6 | 2.14 | 95.72 | 2.14 | 1 | 6.12 | 4.86 | 109 | — | 30 | 1,926 | 500 | 80–145 |
| 7** | 1.7 | 95.2 | 3.1 | 2 | 1.85 | 2.9 | 114 | (¹) | (²) | 2,632 | 466 | 80–185 |
| 8 | 2.72 | 92.5 | 4.78 | 1.75 | 5.75 | 3.35 | 110 | 142.5 | 25 | 1,960 | 230 | 80–150 |
| 9 | 4.0 | 88 | 8 | 2 | 4.75 | 3.5 | 110 | 550 | 110 | 2,100 | 366 | 75–180 |
| 10 | 3 | 88 | 9 | 3 | 6.45 | 2.05 | 111.25 | 705 | 150 | 1,926 | 417 | 75–175 |

*Test Procedure, "Modern Packaging," page 135, Nov. 1952
**Prepared at temperature of 225° C.
¹84 at 225° C.
²121 at 210° C.

EXAMPLE B

In a similar manner as Example A, polyamides are prepared from ethylenediamine and polymeric fat acids from tall oil with the following analysis:
Percent M (Monomeric Fat Acid): 0.5
Percent D (Dimeric Fat Acid): 95.0
Percent T (Trimeric Fat Acid): 4.5
T/M (Trimeric Fat Acid:Monomeric Fat Acid Ratio): 9.0

The data thereon is summarized in the following Table II.

| Eq. Amine Used per Eq. Acid | Acid No. | Amine No. | Ball and Ring M.P., °C. | Visc. at 210° C. Poises | Elong. Percent | Tens. Str., Lbs. | Heat Seal Range, °C. | D° C. |
|---|---|---|---|---|---|---|---|---|
| 1.00 | 1.8 | 3.5 | 123 | 335 | 475 | 3,300 | 85–>225 | >140 |
| .98 | 3.7 | 1.6 | 130 | 807 | 450 | 3,200 | 80–225 | 140 |
| .96 | 6.2 | 0.8 | 110 | 238 | 450 | 2,200 | 80–185 | 105 |
| .94 | 9.0 | 0.7 | 127 | 39 | 475 | 1,700 | 85–160 | 75 |
| .96 | 5.8 | 0.7 | 117 | 132 | 475 | 2,400 | 80–190 | 110 |

EXAMPLE C

In a manner similar to that of Example A, polyamides are prepared from ethylenediamine and polymeric fat acids from tall oil with the following analysis:
Percent M (Monomeric Fat Acid): 1.0
Percent D (Dimeric Fat Acid): 93.0
Percent Trimeric Fat Acid): 6.0
T/M (Trimeric Fat Acid:Monomeric Fat Acid Ratio): 6.0

The data thereon is summarized in the following Table III.

TABLE III

| Eq. Amine Used per Eq. Acid | Acid No. | Amine No. | Ball and Ring S.P., °C. | Visc. at 265° C. Poises | Elong. Percent | Tens. Str., Lbs. |
|---|---|---|---|---|---|---|
| 0.92 | 10.2 | 0.3 | 135 | 18 | 440 | 2,300 |
| 0.84 | 12.6 | 0.21 | 183 | 26 | 410 | 2,160 |
| 0.87 | 12.4 | 0.24 | 164 | 22 | 425 | 2,210 |
| 0.88 | 12.2 | 0.24 | 140 | 21 | 430 | 2,280 |
| 0.89 | 12.2 | 0.27 | 138 | 20 | 430 | 2,290 |
| 0.82 | 12.8 | 0.28 | 200 | 28 | 410 | 2,100 |

EXAMPLE I

PERFUMED POLYMER

Into a vessel associated with a source of heat a quantity of diced Versalon® (prepared according to the procedure of any of Examples A, B or C) amounting to 40.0 parts by weight is heated to about 200° C. at which temperature the resin is a pourable and stirrable body of liquid. A quantity of perfume oil having a floral bouquet with a woody background amounting to 40.0 parts by weight is stirred into the liquid resin until a uniform blend is achieved at which time the mixture is poured into standing cold water to facilitate rapid cooling and solidification to minimize the loss of perfume oil. The resulting product is then formulated into a toroid and placed on a 100 watt electric light bulb according to FIG. 1. The light bulb is then placed into a socket, and electricity is passed through the light bulb. When in standard use at standard brightness, the light bulb will emit perfume into the atmosphere over a period of five use months. Similar results are achieved using the following resins and other perfume oil fragrances:

| | Ball and Ring Softening Point |
|---|---|
| Versalon® 1135 | 135° C. |
| Versalon® 1138 | 138° C. |
| Versalon® 1140 | 140° C. |
| Versalon® 1164 | 164° C. |
| Versalon® 1185 | 183° C. |
| Versalon® 1200 | 120° C. |

In general, it is advantageous to carry out the mixing operation in a closed vessel, preferably a pressure vessel, in order to prevent substantial loss of perfume oil by vaporization. When the final object is made by molding, e.g., injection molding, the perfume oil is preferably introduced directly into the resin in the feed supply line, preferably after the resin has liquified and uniformly blended into the resin therein.

EXAMPLE II

INSECTICIDE-CONTAINING POLYMER

In a vessel associated with a source of heat a quantity of diced Versalon® 1200 polyamide resin (prepared according to the procedures of Example A, B or C)

amounting to 65.0 parts by weight is heated to about 200° C. at which temperature the resin is a pourable and stirrable body of liquid. A quantity of the insecticide mixture amounting to 25.0 parts insecticide (as set forth in Table I) and 20.0 parts diethyl phthalate is stirred into the liquid resin until a uniform blend is achieved at which time the mixture is poured into standing cold water to facilitate rapid cooling and solidification and minimize loss of insecticide product:

TABLE I

| Parts by Weight | Ingredients |
|---|---|
| 66.5% | N,N-diethyl-m-toluamide |
| 20.0% | N-octyl bicycloheptene dicarboximide |
| 5.0% | 2,3:4,5-Bis (2-butylene) tetrahydro-2-furaldehyde |
| 5.0% | Di-n-propyl isocinchomeronate |

The resulting product is a solid having a highly polished surface containing an insecticide which can be emitted on heating polymer at a controllably convenient rate. The product is in the form of a solid solution which lends itself to molding under heat and pressure into objects such as toroids which can be placed on glass light bulbs. Similar effects are achieved using the following polymers and other insecticide materials as well as mixtures of insecticide materials and perfume oil fragrances in an amount of 50:50:

| | Ball and Ring Softening Point |
|---|---|
| Versalon ® 1135 | 135° C. |
| Versalon ® 1138 | 138° C. |
| Versalon ® 1140 | 140° C. |
| Versalon ® 1164 | 164° C. |
| Versalon ® 1185 | 183° C. |
| Versalon ® 1200 | 120° C. |

In general, it is advantageous to carry out the mixing operation in a closed vessel, preferably a pressure vessel, in order to prevent substantial loss of insecticide or insecticide/perfume oil mixture by vaporization. When the final objects are made by molding, e.g., injection molding, the insecticide or insecticide/perfume oil mixture is preferably introduced directly into the resin in the feed supply line, preferably after the resin is liquified and uniformly blended into the resin therein.

EXAMPLE III

POLYMER CONTAINING ANIMAL REPELLENT

In a vessel associated with a source of heat a quantity of diced Versalon ® 1164 (a polyamide resin having a softening point greater than 200° C.) (prepared according to the procedures of Example A, B or C) amounting to 65.0 parts is heated to about 200° C. at which temperature the resin is a pourable and stirrably body of liquid. A quantity of a mixture of methyl-n-nonylketone (65.0 parts by weight) and diethyl phthalate (80.0 parts) is stirred into the liquid resin until a uniform blend is achieved at which time the mixture is poured into standing cold water to facilitate rapid cooling and solidification and minimize loss of methyl-n-nonylketone. The product is in the form of a solid solution which lends itself to spreading as a film on substrates such as glass light bulbs, walls, and the like. The use of the methyl-n-nonylketone in the polyamide resin gives rise to dog and cat repellency when the solid solution is coated on the wall of a building or onto the trunk of a tree. The animal repellency lasts for a period of approximately five months. Similar results are achieved using various other Versalon ® resins and, in addition, mixtures of methyl-n-nonylketone and perfume oil fragrances in the amounts of 50 parts methyl-n-nonylketone and 50 parts perfume oil fragrance.

In general, it is advantageous to carry out the mixing operation in a closed vessel, preferably a pressure vessel, in order to prevent substantial loss of methyl-n-nonylketone and perfume oil by vaporization. When the final coating is made by molding, e.g., injection molding, the methyl-nonyl-ketone is preferably introduced directly into the resin in the feed supply line, preferably after the resin is liquified and uniformly blended into the resin therein.

What is claimed is:

1. A co-solvent free, alcohol free thermoplastic polyamide resin body consisting essentially of from 35% up to 70% by weight of said polyamide resin body of a volatile substance selected from the group consisting of perfume oils, insecticides, odorants, bactericides and animal repellents, the remainder of said thermoplastic polyamide resin body being a fatty polyamide which is a reaction product of ethylene diamine and polymeric fat acids at temperatures in the range of 150°–300° C. employing essentially 1 molar equivalent of amine per molar equivalent of carboxyl group, said polymeric fat acids being polymerized monocarboxylic aliphatic acids having from 8 to 24 carbon atoms, and said polymeric fat acids having a dimeric fat acid content and a ratio of trimeric: monomeric fat acids defined substantially within the area ABC of FIG. 5, said fatty polyamide softening in the range of 10°–15° C. on being heated within the range of 120° C. up to 400° C. and having a sharp decrease in viscosity at temperatures above its softening range, said fatty polyamide having a molecular weight within the range between about 9,000 and 12,000, said resin body being a solid solution.

2. The polyamide resin body of claim 1 wherein the volatile substance is a perfume oil.

3. The polyamide resin body of claim 1 wherein the volatile substance is an animal repellent.

4. The polyamide resin body of claim 1 wherein the volatile substance is an insecticide.

5. The polyamide resin body of claim 1 in which the resin is a coating on a substrate.

6. The polyamide resin body of claim 5 in which the substrate is in the form of an electric light bulb.

7. The polyamide resin body of claim 6 wherein the volatile substance is a perfume oil.

8. The polyamide resin body of claim 6 wherein the volatile substance is an animal repellent.

9. The polyamide resin body of claim 6 wherein the volatile substance is a mixture of insecticide and perfume oil.

10. The polyamide resin body of claim 1 wherein the volatile substance is a mixture of insecticide and perfume oil.

11. The spherical light bulb having fixedly coated thereon a toroid consisting of the thermoplastic polyamide resin body of claim 1.

12. A spherical light bulb having fixedly coated thereon a toroid consisting of the thermopla 'ic resin body of any of claims 2, 3, 4 or 10.

* * * * *